US00PP33596P2

(12) United States Plant Patent
van Aart

(10) Patent No.: US PP33,596 P2
(45) Date of Patent: Nov. 2, 2021

(54) ***HIBISCUS* PLANT NAMED 'GANDINI VAN AART RUBY'**

(50) Latin Name: *Hibiscus syriacus*
Varietal Denomination: Gandini van Aart Ruby

(71) Applicant: Marinus Adrianus Cornelis van Aart, Oudenbosch (NL)

(72) Inventor: Marinus Adrianus Cornelis van Aart, Oudenbosch (NL)

( * ) Notice: Subject to any disclaimer, the term of this patent is extended or adjusted under 35 U.S.C. 154(b) by 0 days.

(21) Appl. No.: 17/103,942

(22) Filed: Nov. 24, 2020

(51) Int. Cl.
*A01H 5/00* (2018.01)
*A01H 6/60* (2018.01)

(52) U.S. Cl.
USPC ..... Plt./257

(58) Field of Classification Search
USPC ..... Plt./226, 257
See application file for complete search history.

*Primary Examiner* — Susan McCormick Ewoldt
*Assistant Examiner* — Karen M Redden
(74) *Attorney, Agent, or Firm* — Penny J. Aguirre

(57) ABSTRACT

A new cultivar of *Hibiscus* plant named 'Gandini van Aart Ruby' that is characterized by its upright, narrow columnar plant habit and its flowers that are dark red-pink in color with a red eye.

2 Drawing Sheets

Botanical classification: *Hibiscus syriacus*.
Cultivar designation: 'Gandini van Aart Ruby'.

CROSS REFERENCE TO A RELATED APPLICATION

This application is related to a European plant breeders' rights application filed on Sep. 25, 2020, application No. 2020/2360. There have been no offers for sale anywhere in the world prior to the effective filing of this Application and no accessibility to one of ordinary skill in the art could have been derived from the printed plant breeder's rights documents.

BACKGROUND OF THE INVENTION

The present invention relates to a new and distinct cultivar of *Hibiscus* plant botanically known as *Hibiscus syriacus* 'Gandini van Aart Ruby' and will be referred to hereafter by its cultivar name, 'Gandini van Aart Ruby'. 'Gandini van Aart Ruby' is a new cultivar of hardy *Hibiscus* grown for use as a landscape plant.

'Gandini van Aart Ruby' was discovered by the Inventor as a chance seedling in a production field of *Hibiscus* plants in Oudenbosch, The Netherlands in August of 2018. The parent plants are unknown.

Asexual propagation of the new cultivar was first accomplished by softwood stem cuttings in Oudenbosch, The Netherlands in August of 2018 by the Inventor. Asexual propagation by grafting and softwood stem cuttings has determined that the characteristics of the new cultivar are stable and are reproduced true to type in successive generations.

SUMMARY OF THE INVENTION

The following traits have been repeatedly observed and represent the characteristics of 'Gandini van Aart Ruby'. These attributes in combination distinguish 'Gandini van Aart Ruby' as a new and distinct cultivar of *Hibiscus*.

1. 'Gandini van Aart Ruby' exhibits an upright, narrow columnar plant habit.
2. 'Gandini van Aart Ruby' exhibits flowers that are dark red-pink in color with a red eye.

'Gandini van Aart Ruby' can be most closely compared to the cultivars 'Gandini van Aart' (U.S. Plant Pat. No. 28,892) and 'Gandini Santiago' (U.S. Plant Pat. No. 25,568). 'Gandini van Aart' is similar to 'Gandini van Aart Ruby' in having an upright and narrow columnar plant habit but differs from 'Gandini van Aart Ruby' in having flowers that are white in color. 'Gandini Santiago' is similar to 'Gandini van Aart Ruby' in having an upright and narrow columnar plant habit and in having flowers that have a red eye but differs from 'Gandini van Aart Ruby' in having lighter purple flowers.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website listings by Plantipp (the breeder's representative) and Ko Noordman (a licensed propagator).

BRIEF DESCRIPTION OF THE DRAWINGS

The accompanying colored photograph illustrates the overall appearance and distinct characteristics of the new *Hibiscus*. The photographs were taken of an 18-month-old plant of 'Gandini van Aart Ruby' as grown outdoors in a 12-cm container in Oudenbosch, The Netherlands.

The photograph in FIG. 1 provides a side view of 'Gandini van Aart Ruby' in bloom.

Figure 1:
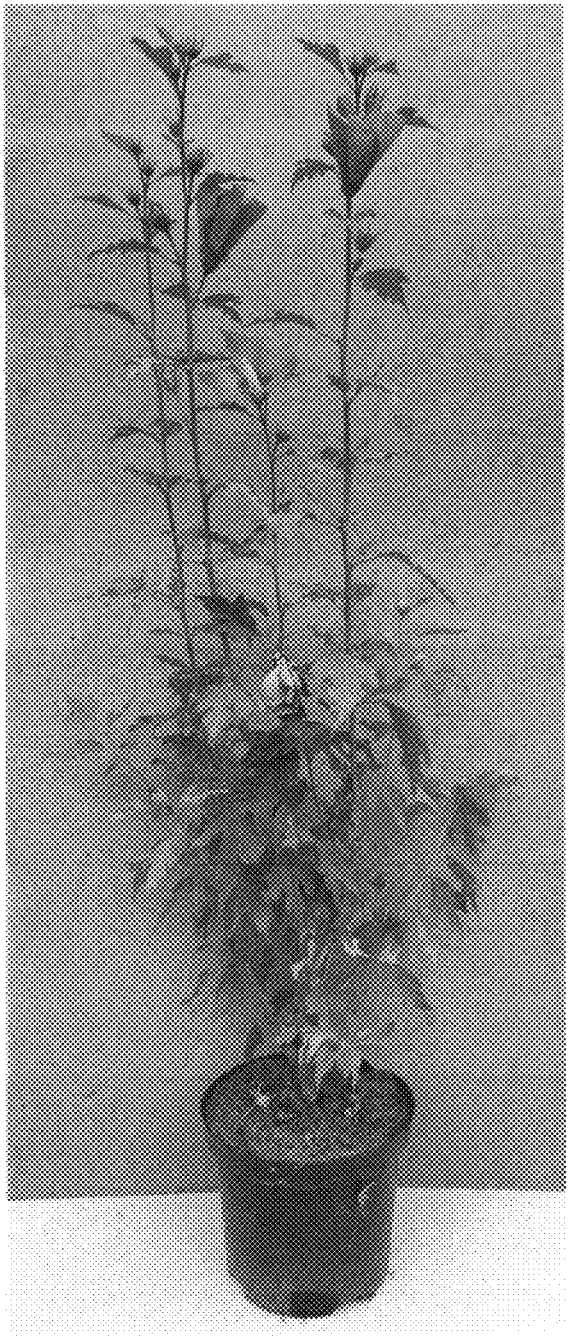
Figure 2:
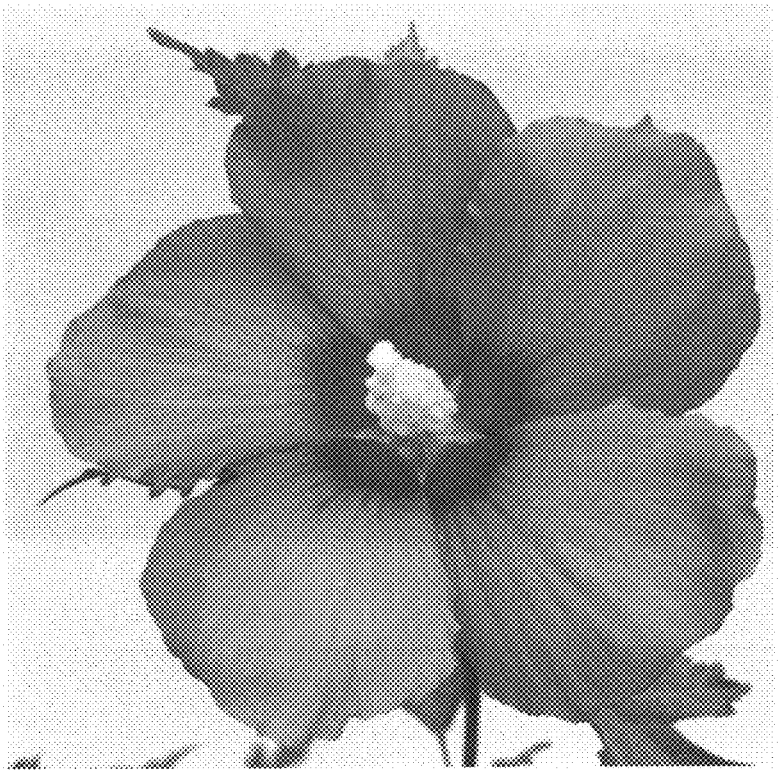

The photograph in FIG. 2 provides a close-up view of a flower of 'Gandini van Aart Ruby'.

Figure 3:
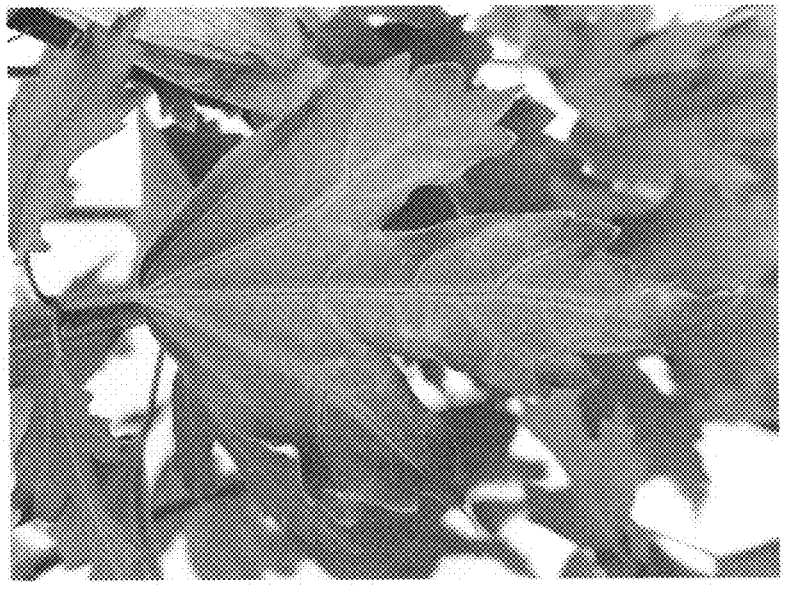

The photograph in FIG. 3 provides a close-up view of a leaf of 'Gandini van Aart Ruby'.

The colors in the photographs are as close as possible with the digital photography and printing techniques utilized and the color codes in the detailed botanical description accurately describe the new *Hibiscus*.

DETAILED BOTANICAL DESCRIPTION OF THE PLANT

The following is a detailed description of 18-month-old plants of the new cultivar as grown outdoors in 12-cm containers in Oudenbosch, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General characteristics:

*Blooming period*.—Mid-summer into early fall in The Netherlands.

*Plant type*.—Herbaceous shrub.

*Plant habit*.—Narrow pyramidal to pyramidal.

*Height and spread*.—Reaches an average of 84 cm in height and 36 cm in width as an 18-month-old plant.

*Hardiness*.—At least in U.S.D.A. Zones 5 to 9.

*Diseases and pests*.—No susceptibility or resistance to diseases has been observed.

*Root description*.—Fibrous.

*Propagation*.—Softwood stem cuttings and grafting.

*Root development*.—Cutting initiate roots in about 6 weeks and fully develop as a young rooted plant in about 3 months.

*Growth rate*.—Moderate to high.

Stem description:

*Shape*.—Round.

*Stem color*.—New growth; 196A, mature wood; 197C.

*Stem size*.—An average of 47 cm in length and 4 mm in diameter.

*Stem surface*.—Glabrous.

*Stem aspect*.—Upright, in an average angle of 70°; varying between 50° and 90° (0°=vertical).

*Stem strength*.—Moderately strong.

*Branching*.—Moderately free branching, an average of 7 lateral branches.

*Internode*.—Average of 4 cm.

Foliage description:

*Leaf shape*.—Overall shape is ovate, three-lobed.

*Leaf division*.—Simple.

*Leaf base*.—Acute.

*Leaf apex*.—Narrowly acute.

*Leaf venation*.—Pinnate, upper surface 137C in color, lower surface 145B in color.

*Leaf margins*.—3-lobed with lobes medium in depth and lobe margins coarsely serrate.

*Leaf attachment*.—Petiolate.

*Leaf arrangement*.—Alternate.

*Leaf orientation*.—Held upright and slightly pendulant.

*Leaf surface*.—Both surfaces are satiny and dull, lower surface; main veins and secondary veins sparsely covered with short adpressed hairs; an average of 1 mm in length and 156D in color.

*Leaf color*.—Young leaves upper and lower surface; 144A, mature leaves upper surface; 137C, mature leaves lower surface; between 144A.

*Leaf size*.—Up to 8 cm in length, and 5 cm in width.

*Leaf quantity*.—About 11 leaves per lateral branch.

*Stipules*.—None present.

*Petioles*.—Average of 1.8 cm in length, 1.5 mm in diameter, upper side 137C in color, lower side 144A in color.

Flower description:

*Inflorescence type*.—Flowers are solitary and semi double with the first flush of bloom and single on later blooms.

*Lastingness of flowers*.—About 4 days, self-cleaning.

*Flower size*.—An average of 5 cm in depth and 9.5 cm in diameter.

*Flower fragrance*.—None.

*Flower shape*.—Rotate, semi-double or single, typical *Hibiscus* shape.

*Flower number*.—Average of 1 per lateral stem.

*Flower aspect*.—Outward to slightly upright.

*Flower bud*.—Elliptic in shape, an average of 2.3 cm in length and 1.3 cm in width, color 138B, glabrous surface.

*Flower attachment*.—Petiolate.

*Petal number*.—Average of 5.

*Petal shape*.—Obovate.

*Petal color*.—Upper surface when opening; 71B with eye zone 53A, lower surface when opening; a blend of 86B, 86C and 86D, base 45A, upper surface when fully open; 71B, eye zone 53A, lower surface when fully open; 71B, base 45A, fading to a blend of 92A and 92B on both surfaces.

*Petal surface*.—Both surfaces smooth, glabrous, matte, moderately velvety.

*Petal margins*.—Entire, slightly wavy.

*Petal arrangement*.—Slightly overlapping.

*Petal apex*.—Rounded.

*Petal size*.—Average of 5.4 cm in length and 3.5 cm in width.

*Petaloids* (*present on semi-double flowers*).—Present at the base of the style, 2 cm in length and 6 mm in width, 2 cm in length and 6 cm in width, average of 8, both surfaces glabrous, matte, and moderately velvety with base glossy, narrow oblong to oblanceolate in shape, entire margins, color of young and mature: upper surface; 71B, eye zone 53A, lower surfaces; 71B, base 45A.

*Sepal number*.—5.

*Sepal shape*.—Elliptic.

*Sepal margin*.—Entire.

*Sepal size*.—Average of 1.7 cm in length and 7 mm in width.

*Sepal aspect*.—Rotate, lower 50% fused.

*Sepal surface*.—Both sides matte and glabrous.

*Sepal apex*.—Acute.

*Sepal base*.—Broad cuneate (fused).

*Sepal color*.—Young and mature upper surfaces; between 145B, young and mature lower surfaces; 145A.

*Calyx*.—Rotate in shape, average of 2.1 cm in length and 1.6 cm in diameter.

*Peduncles*.—Average of 2.3 cm in length, 2 mm in diameter, average angle of 40°, moderately strong, 144A in color, surfaces are glabrous.

*Pedicels*.—Not present, flowers emerge from terminals of stem and are solitary.

*Bracts*.—At the base of each flower is a ring of bracts adpressed against the sepals, average of 7, linear in shape, average of 1.5 cm in length and 1.5 mm in width and 137C in color, both surfaces glabrous.

*Stipules*.—Not present.

Reproductive organs:

*Gynoecium*.—Pistil; 1, average of 3.7 cm in length, stigmas; club-shaped, an average of 5 and 155A in color, style; 3.5 cm in length and 155C in color, ovary; 145C in color and completely covered by the base of the style.

*Androecium*.—Stamens; average of 50, stamens are clustered and implanted and clustered in style, anthers; dorsifixed and broad kidney shaped, 1.5 mm in length and 155A in color; filaments; 2.5 mm in length and 158B to 158C in color, pollen; abundant in quantity and 11C in color.

*Fruit/seeds*.—Sterile; no fruit or seeds are produced.

It is claimed:

1. A new and distinct cultivar of *Hibiscus* plant named 'Gandini van Aart Ruby' as herein illustrated and described.

* * * * *